United States Patent [19]

Ellingboe et al.

[11] Patent Number: 4,966,975

[45] Date of Patent: Oct. 30, 1990

[54] PROCESSES FOR THE PREPARATION OF NOVEL NAPHTHALENYLMETHYL-3H-1,2,3,5-OXA-THIADIAZOLE 2-OXIDES USEFUL AS ANTIHYPERGLYCEMIC AGENTS

[75] Inventors: John W. Ellingboe; Jehan F. Bagli, both of Princeton; Thomas R. Alessi, Monmouth Junction, all of N.J.

[73] Assignee: American Home Product

[21] Appl. No.: 341,615

[22] Filed: Apr. 21, 1989

[51] Int. Cl.[5] .............................................. C07D 291/04

[52] U.S. Cl. ...................................................... 548/122

[58] Field of Search .......................................... 548/122

[56] References Cited

U.S. PATENT DOCUMENTS 3,118,903 1/1964 Schmitt ................................ 548/122

*Primary Examiner*—Robert Gerstl

[57] ABSTRACT

This invention relates to the processes for the production of novel [(substituted naphthalenyl)methyl]-3H-1,2,3,5-oxathiadiazole 2-oxides. The compounds have pharmaceutical properties which render them beneficial for the treatment of diabetes mellitus and associated conditions.

3 Claims, No Drawings

PROCESSES FOR THE PREPARATION OF NOVEL NAPHTHALENYLMETHYL-3H-1,2,3,5-OXATHIADIAZOLE 2-OXIDES USEFUL AS ANTIHYPERGLYCEMIC AGENTS

BACKGROUND OF THE INVENTION

This invention relates to the processes for the preparation of novel [(substituted naphthalenyl)methyl]-3H-1,2,3,5-oxathiadiazole 2-oxides. The compounds have pharmaceutical properties which render them beneficial for the treatment of diabetes mellitus and associated conditions.

The serious complications of diabetes mellitus such as nephropathy, retinopathy, neuropathy and cataract are all associated with an excessive amount of blood glucose. The major therapeutic objective is therefore the normalization of blood glucose, both in the fasting and postprandial situations.

The therapeutic approaches to the treatment of Non-Insulin Dependent Diabetes Mellitus (NIDDM, Type II) involve the use of diet, insulin or orally active hypoglycemic agents. Presently, such agents are chosen (a) from sulfonylureas such as chloropropamide, glyburide and others or (b) biguanides such as metformin and related products. Both these groups of agents have serious disadvantages. Sulfonylureas, upon chronic treatment, lose their effectiveness. In contrast, biguanides suffer from a serious side effect, that causes lacticacidosis.

More recently, oxazolidinedione (U.S. Pat. No. 4,342,771) and thiazolidinedione (European Patent Application No. 117,035) derivatives have been described as useful hypoglycemic agents. U.S. Pat. No. 4,461,902 discloses substituted 5-[(4-cyclohexyl-methoxyphenyl)-methyl]thiazolidine-2,4-diones of formula

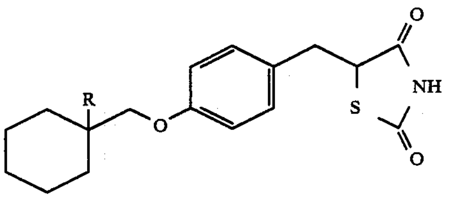

wherein R is methyl (ciglitazone) and related analogues as hypoglycemic agents.

This invention relates to processes for the production of novel [(substituted naphthalenyl)methyl]-3H-1,2,3,5-oxathiadiazole 2-oxides of the general formula (I):

(I)

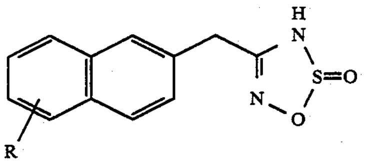

wherein R is hydrogen, lower alkyl containing 1 to 6 carbon atoms, alkoxy containing 1 to 6 carbon atoms, or halogen; and the pharmaceutically acceptable salts thereof having utility as antidiabetic agents.

The oxathiadiazole 2-oxide portion of the compounds of the present invention can exist in more than one tautomeric form. For clarity, only one of the tautomers is represented in the generic formula (I) above. The possible tautomeric forms are listed below:

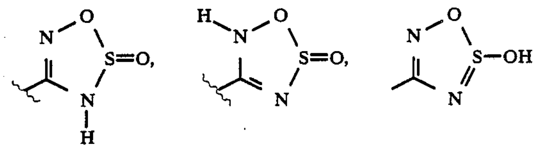

All of said tautomers are included in the present invention. The actual tautomeric form which the compounds of the present invention assume is not known.

The compounds of this invention are useful as antidiabetic agents for the reduction of blood/plasma sugar levels or for the treatment and/or prevention of diabetic complications and as antihyperlipidemic and antihyperinsulinemic agents.

DETAILED DESCRIPTION OF THE INVENTION

The naphthalenylmethyl-3H-1,2,3,5-oxathiadiazole 2-oxides of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered orally in solid form containing such excipients as starch, milk, sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the naphthalenylmethyl-3H-1,2,3,5-oxathiadiazole 2-oxides will vary with the form of administration and the particular compound chosen. Furthermore, it will vary with the particular host under treatment. Generally, treatment is initiated with small dosages substantially less than the optimal dose of the compound. Therefore, the dosage is increased by small increments until efficacy is obtained. In general, the compounds of this invention are most desirably administered at a concentration level that will generally afford effective results without causing any harmful or deleterious side effects.

For oral administration (or as a suppository) to an adult patient, a preferred level of dosage ranges from about 0.01 to 10 mg/kg body weight/day. For parenteral administration to an adult patient, a preferred level of dosage ranges from about 0.005 to 10 mg/kg body weight/day, once daily or divided into 2 to 4 times a week.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The naphthalenylmethyl-3H-1,2,3,5-oxathiadiazole 2-oxides can also be used in combination with dietary restriction, insulin, sulfonylureas, such as chloropropamide and glyburide, biguanides, such as metformin, aldose reductase inhibitors or hypolipidemic agents to produce a beneficial effect in the treatment of diabetes mellitus. In this instance, commercially available insulin preparations or agents exemplified above are suitable. The compounds hereof can be administered sequentially or simultaneously with insulin or the above exemplified agents. Suitable methods of administration, compositions and doses of the insulin preparations or the above exemplified agents are described in medical textbooks; for instance, "Physicians' Desk Reference", 36 ed., Medical Economics Co., Oradell, N.J., U.S.A., 1982.

The processes of the present invention are outlined in Schemes I, II, and III below:

Scheme I: Process 1

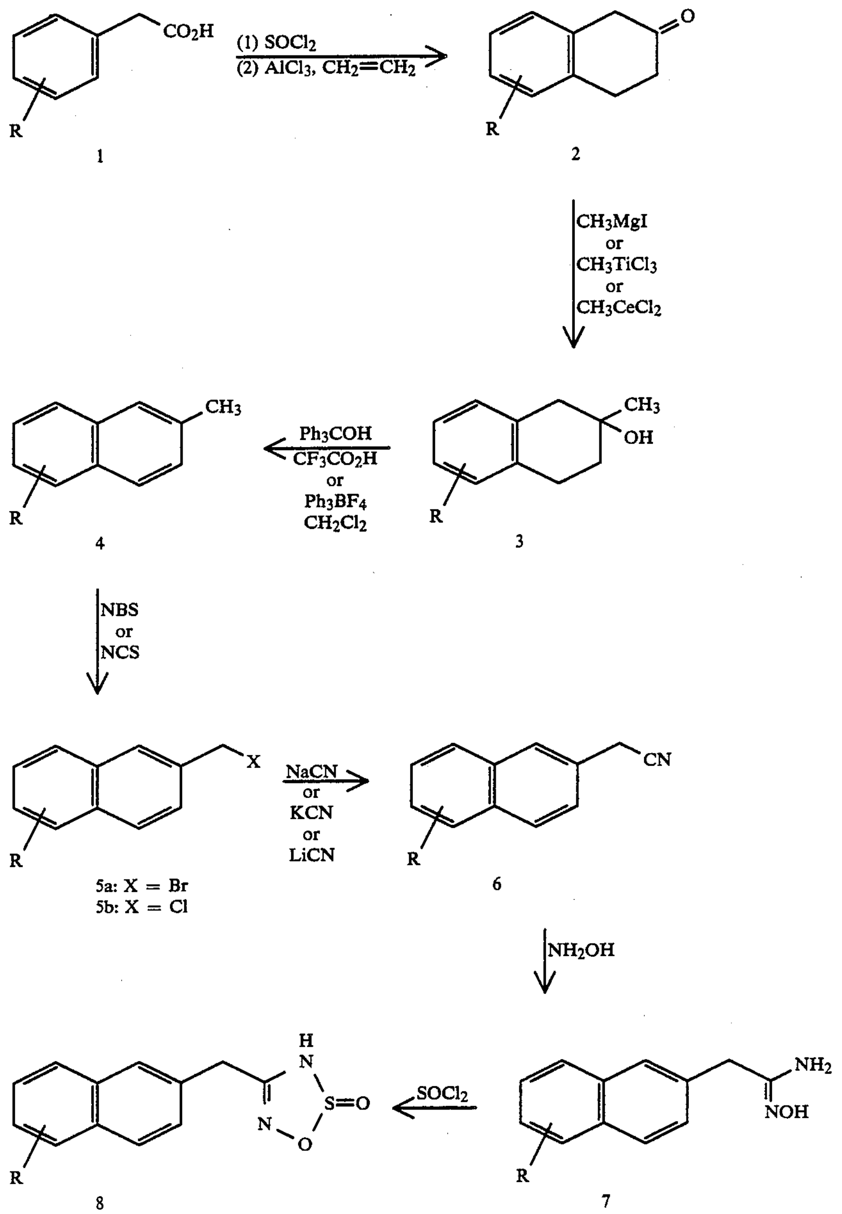

5a: X = Br
5b: X = Cl wherein R is as defined above.

Scheme II: Process 2
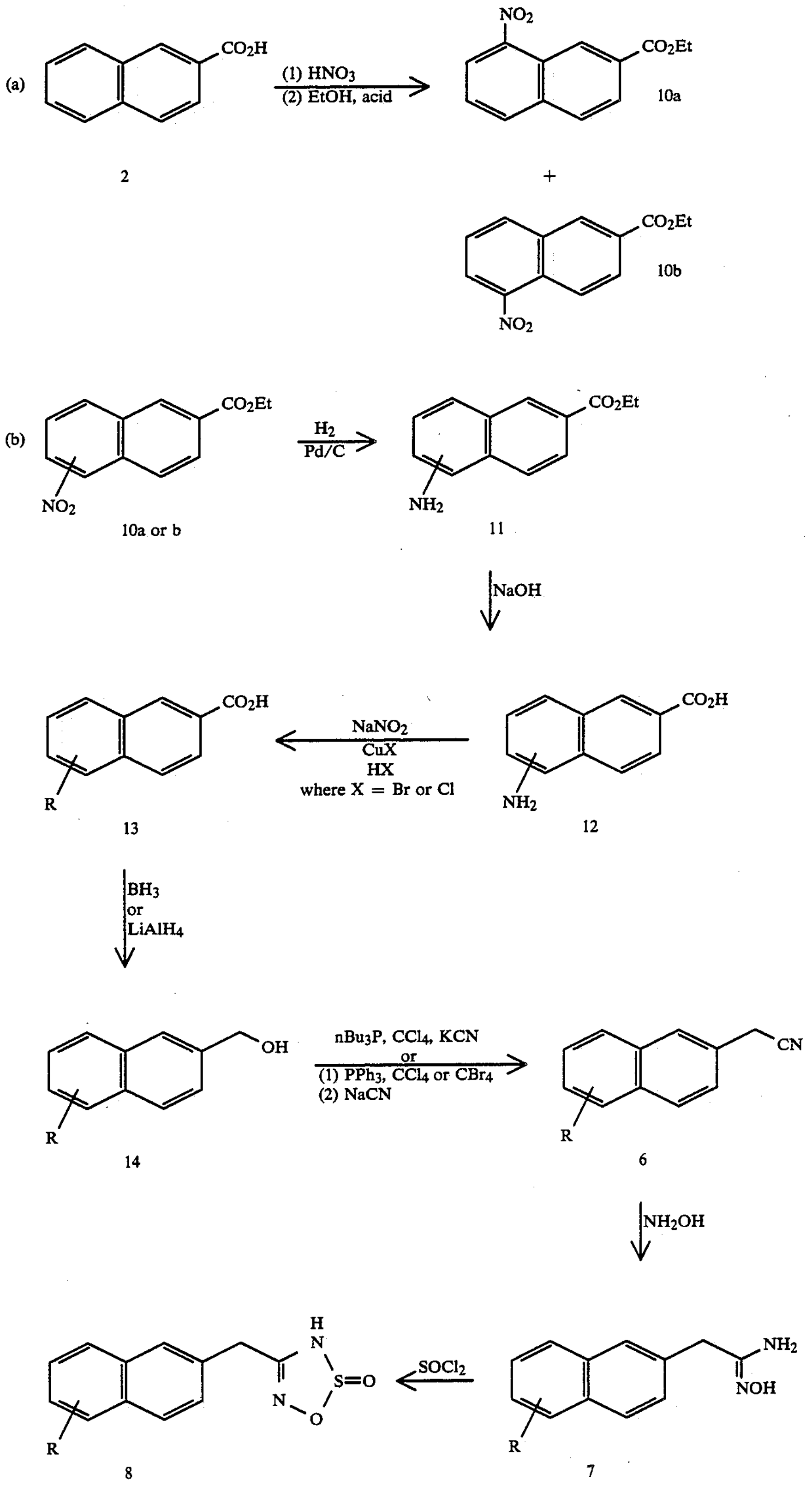
wherein R is Br or Cl, in position 5 or 8.

Scheme III: Process 3

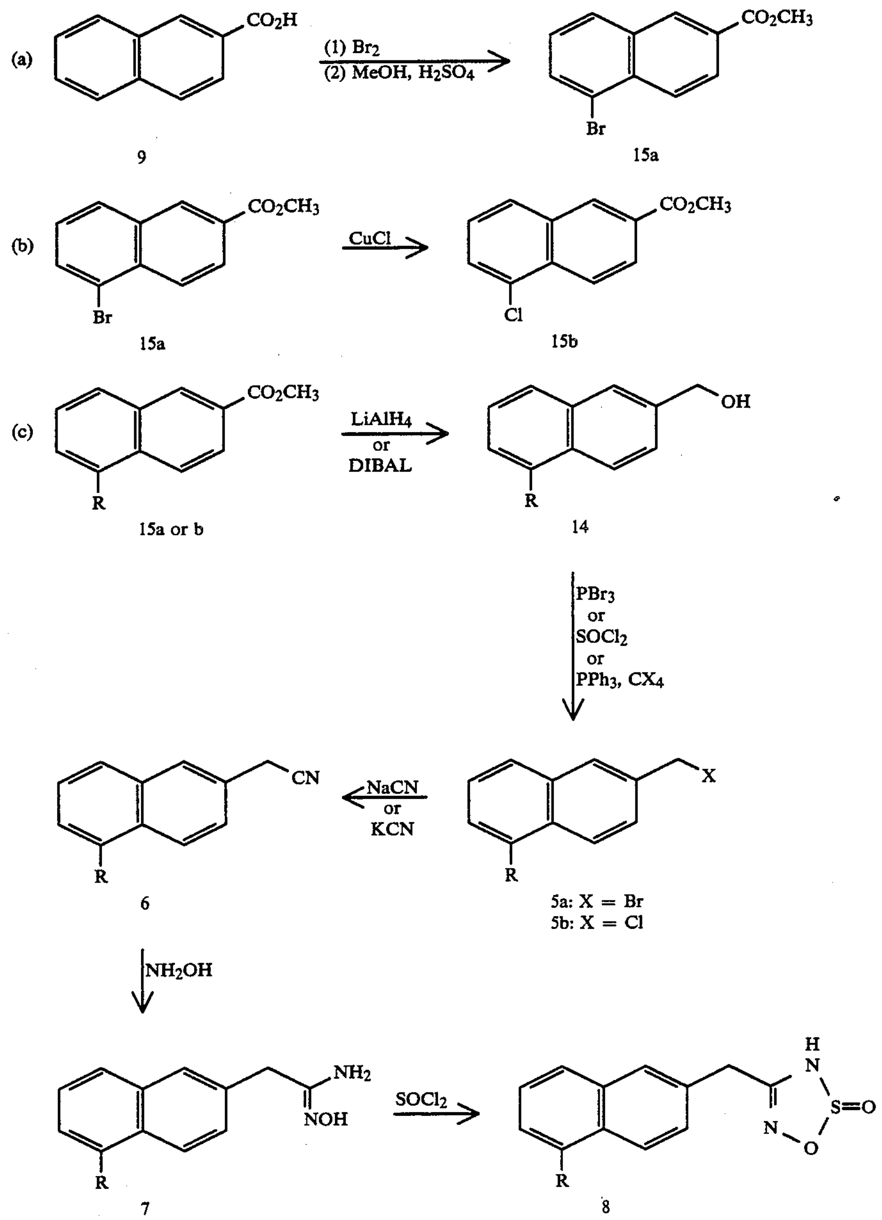

wherein R is Br or Cl.

Process 1

Process 1 (Scheme I) starts with a substituted phenylacetic acid (1) wherein the substituent R is as defined above, which is converted to the corresponding acid chloride with thionyl chloride in halogenated solvents such as methylene chloride, chloroform or carbon tetrachloride at ambient temperature to reflux. The acid chlorides are transformed into 2-tetralones (2) with a Lewis acid such as aluminum trichloride or titanium tetrachloride and ethylene. The reaction is performed in solvents commonly used in Friedel-Crafts reactions such as methylene chloride or carbon disulfide, at low temperatures (−40° to 5° C.). The carbonyl groups of the tetralones (2) are methylated with an organometallic species such as methylmagnesium iodide, methyltrichlorotitanium or methyldichlorocerium in inert solvents such as methylene chloride, tetrahydrofuran, diethyl ether or toluene at low temperatures (−70° to 0° C.). Aromatization of the alcohols (3) is achieved with trityl alcohol/trifluoroacetic acid or trityl fluoroborate/methylene chloride at ambient temperature to reflux. The resulting 2-methylnaphthalenes (4) are halogenated with a N-halosuccinimide in carbon tetrachloride at reflux. The halogen introduced in the preceding step is displaced with cyanide using lithium, sodium or potassium cyanide in a polar solvent such as dimethyl sulfoxide, dimethylformamide, ethanol or acetonitrile, with or without added water, at ambient temperatures to reflux. The nitriles (6) are converted to the amidoximes (7) with hydroxylamine in a polar solvent such as methanol or dimethyl sulfoxide at ambient temperatures to reflux. Finally, the oxathiadiazoles (8) are obtained by treatment of the amidoximes (7) with thionyl chloride and an amine base such as pyridine or triethylamine in organic solvents such as methylene chloride or tetrahydrofuran at low temperatures (−40° to 5° C.). Alternatively, the oxathiadiazoles (8) can be obtained by treatment of the amidoximes (7) with thionyl chloride in the absence of base in solvents such as benzene or toluene at ambient temperatures to reflux.

Process 2

2-Naphthoic acid (9) is the starting material for Process 2 (Scheme II). Nitration with nitric acid at 20° to 80° C. and sulfuric acid catalyzed esterification of the crude nitration reaction mixture with ethanol yields a mixture of 5- and 8-nitronaphthoic acid ethyl esters (10a and 10b, approximately 1:1). Separation of the two isomers is achieved by recrystallization and chromatography on silica gel.

The nitro compounds (10a and b) are reduced by catalytic hydrogenation to the corresponding aminonaphthoates (11). Hydrolysis of the ethyl esters with aqueous hydroxide yields the aminonaphthoic acids (12). The halogen compounds (13) are obtained by diazotization of the aminonaphthoic acids (12) with sodium nitrite in sulfuric acid and acetic acid at 5° C. to ambient temperature and a subsequent Sandmeyer reaction with either cuprous chloride in concentrated hydrochloric acid or cuprous bromide in concentrated hydrobromic acid at ambient temperatures to 100° C. Reduction of the halonaphthoic acids (13) is performed with a reducing agent such as borane or lithium aluminum hydride in an inert solvent such as toluene, tetrahydrofuran or ether at 0° C. to reflux. The resulting alcohols (14) are converted to the naphthalenylacetonitriles (6) via a one or two step sequence. The two step sequence procedes via a halomethylnaphthalene (5) prepared with triphenylphosphine and either carbon tetrachloride or carbon tetrabromide in an organic solvent such as methylene chloride, tetrahydrofuran or acetonitrile; or with thionyl chloride and zinc chloride in ether, tetrahydrofuran or dioxane; or with phosphorus tribromide in ether or methylene chloride, all at ambient temperatures to reflux. The second step of the sequence for conversion of the halomethylnaphthalenes (5) to the naphthalenylacetonitriles (6) is the same as described in Process 1 above. Alternatively, the nitriles (6) can be obtained from alcohols (14) in a one-step procedure with a trialkyl or triarylphosphine, carbon tetrachloride, potassium cyanide and the crown ether 18-crown-6 in acetonitrile at ambient temperatures. The remaining two steps in Process 2, conversion of the nitriles (6) to amidoximes (7) and subsequent formation of the oxathiadiazoles (8) are the same as described in Process 1 above.

Process 3

As in Process 2,2-naphthoic acid (9) is utilized as the starting material in Process 3 (Scheme III). Bromination with bromine in refluxing acetic acid and acid catalyzed esterification with methanol yields 5-bromo-2-naphthoic acid methyl ester (15) (Scheme III, step a)). The 5-bromonaphthalene (15a) can be converted to the 5-chloronaphthalene (15b) with cuprous chloride in a polar solvent such as dimethyl sulfoxide, dimethylformamide or N-methylpyrrolidinone at ambient temperatures to reflux. The halonaphthalenes (15a and b) are reduced to the alcohols 14 with a reducing agent such as lithium aluminum hydride or diisobutyl aluminum hydride in an inert solvent such as toluene, tetrahydrofuran, hexane or ether at 0° C. to ambient temperatures. The remaining steps in Process 3 for conversion of the alcohols (14) to the oxathiadiazoles (8) are the same as those described for Process 2 above.

A preferred process of the present invention is illustrated by the production of 4-[(8-bromo-2-naphthalenyl)methyl]-3H-1,2,3,5-oxathiadiazole 2-oxide set forth in Scheme IV.

Scheme IV

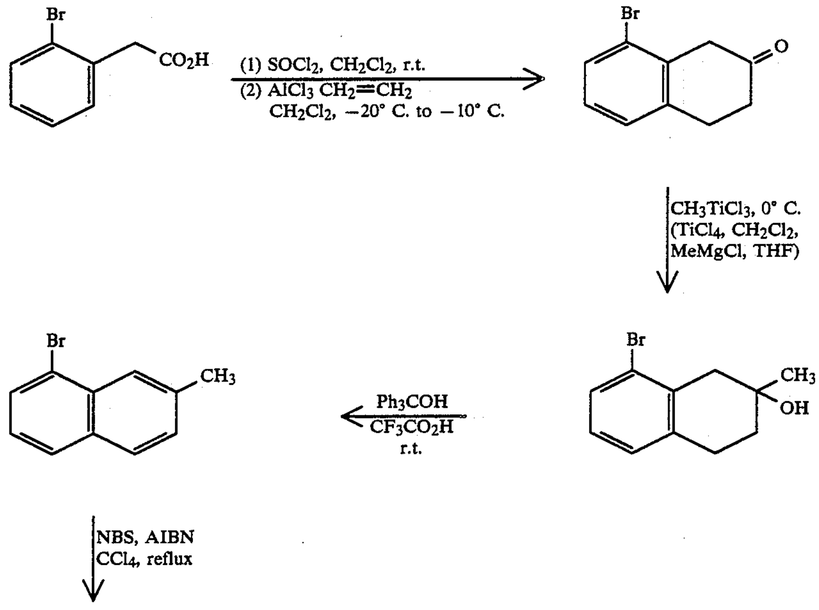

-continued
Scheme IV
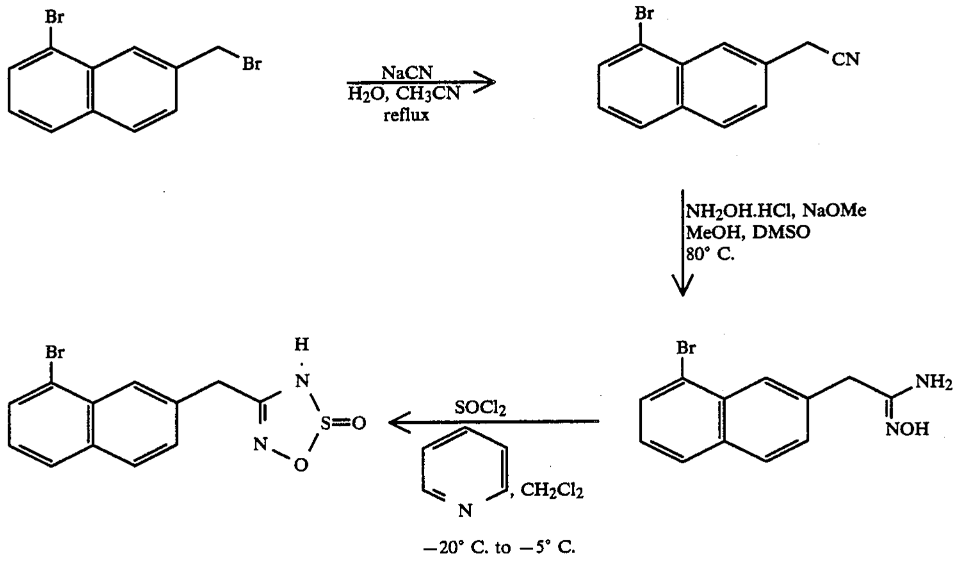
A still further preferred process of the present invention is illustrated by the production of 4-[(5-chloro-2-naphthalenyl)methyl]-3H-1,2,3,5-oxathiadiazole 2-oxide set forth in Scheme V.
Scheme V
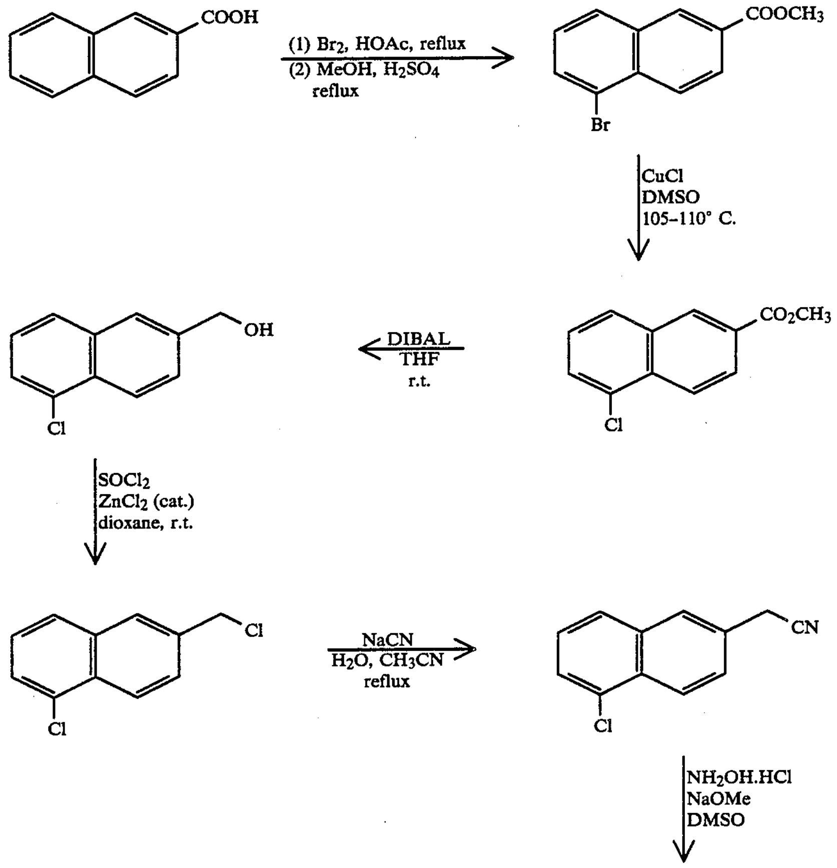

-continued

Scheme V

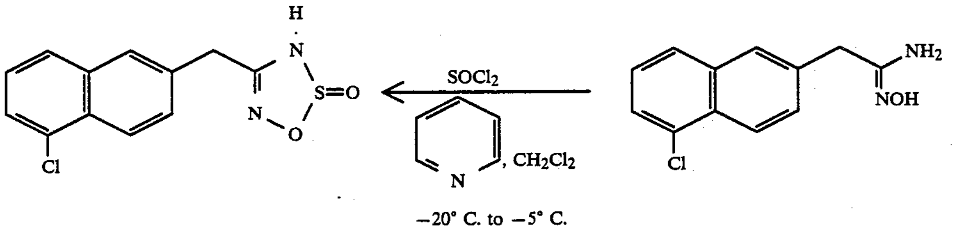

The chemical bases which are used as reagents in this invention to prepare the aforementioned pharmaceutically acceptable salts are those which form non-toxic salts with the various herein described naphthalenylmethyl-3H-1,2,3,5-oxathiadiazole 2-oxides. These particular non-toxic base salts are of such a nature that their cations are said to be essentially non-toxic in character over the wide range of dosage administered. Examples of such cations include those of sodium, potassium, calcium and magnesium. These salts may be prepared by mixing organic solutions of the naphthalenylmethyl-3H-1,2,3,5-oxathiadiazole 2-oxides in alcohol and the desired alkali metal alkoxide together and then isolating the resulting salts by removal of the solvent and filtration with a non-polar solvent. Stoichiometric quantities of reagents must be employed in order to ensure completeness of reaction and maximum production yields with respect to the desired final product.

The following examples further illustrate the present invention.

EXAMPLE 1

4-[(8-Bromo-2-naphthalenyl)methyl]-3H-1,2,3,5-oxathiadiazole 2-Oxide

Step (1) Preparation of Ethyl 8-Amino-2-naphthoate

According to the procedure of W. Adcock, et al. *Aust. J. Chem.* 18, 1351 (1965), a suspension of ethyl 8-nitro-2-naphthoate prepared according to Price, et al. *J. Am. Chem. Soc.* 74, 3652 (1952) (8.2 g, 0.033 mol) in ethanol (240 mL) was hydrogenated at 50 psi over 10% Pd/C (820 mg) for 4 hours. The mixture was filtered through Solka floc® and concentrated. Recrystallization of the residue from EtOH/$H_2O$ gave a yellow solid (5.2 g, 72%), m.p. 97°-98° C.

NMR ($CDCl_3$, 200 MHz): δ1.44 (t, J=7.3 Hz, 3H), 4.35 (br s, 2H), 4.44 (q, J=7.3 Hz, 2H), 6.80 (d, J=7.3 Hz, 1H), 7.30 (d, J=7.3 Hz, 1H), 7.39 (dd, J=7.3 Hz, 7.3 Hz, 1H), 7.81 (d, J=8.6 Hz, 1H), 8.03 (d, J=8.6 Hz, 1H), 8.64 (s, 1H).

Step (2) Preparation of 8-Amino-2-naphthoic Acid

According to the procedure of W. Adcock, et al. *Aust. J. Chem.* 18, 1351 (1965), a mixture of ethyl 8-amino-2-naphthoate (5.2 g, 0.024 mol), 1N NaOH (48 mL, 0.048 mol), and dioxane (50 mL) was stirred at room temperature for 3 hours. The dioxane was removed under reduced pressure, and the aqueous phase was diluted with $H_2O$ (100 mL) and extracted with ether. Neutralization with acetic acid produced a yellow precipitate which was collected by filtration (3.2 g, 71%), m.p. 221°-223° C.

NMR (DMSO-$d_6$, 200 MHz): δ6.05 (br s, 2H), 6.72 (d, J=7.9 Hz, 1H), 7.09 (d, J=7.9 Hz, 1H), 7.31 (dd, J=7.9 Hz, 7.9 Hz, 1H), 7.76 (d, J=8.8 Hz, 1H), 7.85 (d, J=8.8 Hz, 1H), 8.78 (s, 1H).

Step (3) Preparation of 8-Bromo-2-naphthoic Acid

According to the procedure of W. Adcock, et al. *Aust. J. Chem.* 18, 1351 (1965) and H. H. Hodgson, et al. *J. Chem. Soc.*, 1620 (1933), to a cooled (10° C.), stirred solution of $NaNO_2$ (1.24 g, 0.0179 mol) in $H_2SO_4$ (16.1 mL) and HOAc (14.9 mL) [prepared by adding $NaNO_2$ to cooled (10° C.) $H_2SO_4$, heating to dissolve, recooling, and adding HOAc] was added a solution of 8-amino-2-naphthoic acid (2.80 g, 0.0150 mol) in HOAc (50 mL) over 10 minutes. The resulting solution was added slowly (over 10 minutes) to a heated (60° C.), stirred solution of CuBr (9.44 g, 0.0658 mol) in concentrated HBr (90 mL). The mixture was warmed to 90° C. for 10 minutes, cooled, diluted with $H_2O$ (200 mL) and filtered to give a green solid, 3.4 g. The crude product was combined with similarly prepared material (450 mg) and recrystallized from EtOH to give an off-white solid (2.3 g, 55%), m.p. 265°-266° C.

NMR (DMSO-$d_6$, 400 MHz): δ7.57 (dd, J=8.2 Hz, 7.5 Hz, 1H), 7.98 (dd, J=7.5 Hz, 1.0 Hz, 1H), 8.07 (m, 2H), 8.11 (d, J=8.5 Hz, 1H), 8.79 (s, 1H), 11.67 (br s, 1H).

MS: m/e 250 (95%), 126 (100%).

Step (4) Preparation of 8-Bromo-2-hydroxymethylnaphthalene

To a cooled (0° C.), stirred suspension of 8-bromo-2-naphthoic acid (2.25 g, 8.96 mmol) in THF (12 mL) was added $BH_3$.THF (1M in THF, 12.5 mL, 12.50 mmol) over 20 minutes. The cooling bath was removed and stirring was continued at room temperature overnight. The mixture was recooled to 0° C. and saturated aqueous $K_2CO_3$ (8 mL) was added. $H_2O$ (10 mL) was added and the mixture was extracted with ether. The combined extracts were washed with saturated aqueous NaCl, dried ($MgSO_4$) and concentrated. The crude product was recrystallized from ether/hexane to give an off-white solid (1.70 g, 80%), m.p. 110°-111° C.

NMR ($CDCl_3$, 200 MHz): δ4.91 (d, J=5.3 Hz, 2H), 7.31 (dd, J=8.0 Hz, 8.0 Hz, 1H), 7.55 (dd, J=8.7 Hz, 1.6 Hz, 1H), 7.82 (m, 3H), 8.19 (s, 1H).

Step (5) Preparation of 8-Bromo-2-naphthalenylacetonitrile

According to the procedure of A. Mizuno, et al. *Synthesis* 1007 (1980), a mixture of 8-bromo-2-hydroxymethylnaphthalene (1.70 g, 7.17 mmol), KCN (0.93 g, 14.34 mmol) and 18-crown-6 (0.19 g, 0.72 mmol) in acetonitrile (24 mL) was stirred at room temperature for 15 minutes. A mixture of n-$Bu_3P$ (1.60 g, 7.89 mmol) and acetonitrile (7 mL) was added. The mixture was cooled to 0° C., and a solution of $CCl_4$ (1.21 g, 7.89 mmol) in acetonitrile (7 mL) was added. The resulting mixture was stirred at room temperature for two days.

Ether (300 mL) was added and the mixture was washed with 10% aqueous citric acid (150 mL). $CCl_4$ (20 mL) was added and the mixture was washed with $H_2O$ (2×150 mL); saturated aqueous NaCl (150 mL), dried ($MgSO_4$), and concentrated. The crude material was purified by flash chromatography (eluant EtOAc/hexane (5:95), to EtOAc/hexane (20:80)) to give a yellow solid (1.13 g, 64%), m.p. 55°-56° C.

NMR ($CDCl_3$, 200 MHz): δ3.96 (s, 2H), 7.35 (dd, J=8.3 Hz, 7.2 Hz, 1H), 7.48 (dd, J=8.6 Hz, 2.0 Hz, 1H), 7.83 (m, 3H), 8.18 (d, J=1.2 Hz, 1H).

IR($CCl_4$, $cm^{-1}$): 2255 (CN).

Step (6) Preparation of N'-Hydroxy-2-(8-bromonaphthalenyl)ethanimidamide

A mixture of NaOMe (25 wt % in MeOH, 1.6 ml, 6.83 mmol), MeOH (3 mL), and hydroxylamine hydrochloride (0.47 g, 6.83 mmol) was heated for 30 minutes.

8-Bromo-2-naphthalenylacetonitrile (1.12 g, 4.55 mmol) and MeOH (5 mL) were added and heating was continued for 24 hours. The mixture was concentrated, and suspended in $H_2O$ (40 mL) and ether (2 mL). The off-white solid was collected by filtration and triturated with ether to give the title compound (790 mg, 62%), m.p. 123°-125° C.

NMR (DMSO-$d_6$, 200 MHz): δ3.50 (s, 2H), 5.50 (s, 2H), 7.38 (dd, J=7.6 Hz, 7.6 Hz, 1H), 7.54 (d, J=8.3 Hz, 1H), 7.85 (d, J=7.6 Hz, 1H), 7.89 (m, 2H), 8.02 (s, 1H), 8.96 (s, 1H).

Step (7) Preparation of 4-[(8-Bromo-2-naphthalenyl)methyl]-3H-1,2,3,5-oxathiadiazole 2-Oxide To a cooled (0° C.), stirred suspension of N'-hydroxy-2-(8-bromonaphthalenyl)ethanimidamide (437 mg, 1.56 mmol) in pyridine (248 mg, 3.13 mmol) and $CH_2Cl_2$ (2 mL) was added thionyl chloride (205 mg, 1.72 mmol). The resulting solution was stirred for 20 minutes, concentrated, and partitioned between ether and water. The organic phase was dried ($MgSO_4$) and concentrated. The product was recrystallized from ethanol/ether to give a white solid (123 mg, 24%), m.p. 157°-158° C.

NMR (DMSO-$d_6$, 400 MHz): δ4.20 (s, 2H), 7.43 (m, 1H), 7.52 (dd, J=8.4 Hz, 1.6 Hz, 1H), 7.89 (dd, J=7.6 Hz, 0.9 Hz, 1H), 7.97 (d, J=8.4 Hz, 1H), 7.99 (d, J=8.4 Hz, 1H), 8.10 (s, 1H), 11.53 (br s, 1H).

IR (KBr, $cm^{-1}$): 3450 (NH).

MS: m/e 324 (17%), 139 (100%).

Anal. Calcd for $C_{12}H_9BrN_2O_2S$: C, 44.32; H, 2.79; N, 8.61%. Found: C, 44.01; H, 2.60; N, 8.62%.

The compound 4-[(8-bromo-2-naphthalenyl)methyl]-3H-1,2,3,5-oxathiadiazole 2-oxide may also be prepared by the following alternate process.

Step (1) Preparation of 8-Bromo-2-tetralone

According to the procedure of A. Rosowsky, et al. *J. Org. Chem.* 26, 4232 (1961), to a stirred solution of 2-bromophenylacetic acid (150.0 g, 0.698 mol) in $CH_2Cl_2$ (500 mL) was added DMF (1 mL) and thionyl chloride (102 mL, 1.395 mol). The mixture was left standing for 18 hours, concentrated, and azeotroped with $CCl_4$ (3×100 mL). To a cooled (−20° C.) mechanically stirred suspension of $AlCl_3$ (186.0 g, 1.395 mol) in $CH_2Cl_2$ (1000 mL) was added a solution of 2-bromophenylacetyl chloride (163 g, 0.698 mol) in $CH_2Cl_2$ (350 mL) over 30 minutes. Ethylene was bubbled into the mixture for 1 hour (at −15° C. for 45 minutes then at −10° C. for 15 minutes, total ethylene used: 69.2 g). Stirring at −10° C. was continued for 15 minutes and the mixture was poured onto ice (1200 g). The layers were separated and the organic phase was washed with $H_2O$, saturated aqueous $NaHCO_3$, brine, dried ($MgSO_4$) and concentrated. The resulting yellow solid was taken up in $CH_3CN$ (1000 mL), washed with pentane (2×500 mL) to remove polyethylene, and concentrated to give a yellow solid (146.2 g, 93%). An analytical sample was obtained by recrystallization from ether/hexane.

8-Bromo-2-tetralone is not stable in solution and should be stored cold under $N_2$.

NMR (DMSO-$d_6$, 400 MHz): δ2.48 (t, J=6.6 Hz, 2H), 3.06 (t, J=6.6 Hz, 2H), 3.60 (s, 2H), 7.15 (dd, J=7.6 Hz, 7.6 Hz, 1H), 7.29 (d, J=7.6 Hz, 1H), 7.50 (d, J=7.6 Hz, 1H).

IR (KBr, $cm^{-1}$): 1710 (C=O).

MS: m/e 224 ($M^+$).

Anal. Calcd for $C_{10}H_9BrO$: C, 53.36; H, 4.03%. Found: C, 53.18, H, 3.74%.

Step (2) Preparation of 8-Bromo-2-hydroxy-2-methyl-1,2,3,4-tetrahydronaphthalene According to the procedure of M. T. Reetz, et al., *Tetrahedron* 42, (11), 2931 (1986), to a cooled (−30° C.) stirred solution of $TiCl_4$ (109.9 g, 0.580 mol) in $CH_2Cl_2$ (580 mL) was added 3.0M $CH_3MgCl$/THF (193 mL, 0.580 mol) over 35 minutes. To the resulting dark purple mixture was added a solution of 8-bromo-2-tetralone (108.7 g, 0.483 mol) in $CH_2Cl_2$ (150 mL) over 30 minutes. The mixture was warmed to 0° C. After 2 hours, the mixture was poured onto ice (1000 g). The layers were separated, and the organic phase was washed with 2N HCl, brine, dried ($MgSO_4$), and concentrated to give a brown solid (117.0 g, 100%). This material was used directly in the next reaction without further purification. An analytical sample was prepared from 300 mg of previously prepared material by recrystallization from hexane, m.p. 73°-74° C.

NMR (DMSO-$d_6$, 400 MHz): δ1.24 (s, 3H), 1.58 (m, 1H), 1.70 (m, 1H), 2.57 (d, J=17.0 Hz, 1H), 2.64 (m, 1H), 2.70 (d, J=17.0 Hz, 1H), 2.95 (m, 1H), 4.48 (s, 1H), 7.03 (dd, J=7.6 Hz, 7.6 Hz, 1H), 7.11 (d, J=7.6 Hz, 1H), 7.39 (d, J=7.6 Hz, 1H).

IR (KBr, $cm^{-1}$): 3350 (OH).

MS: m/e 240 ($M^+$), 222 ($M^+$-$H_2O$).

Anal. Calcd for $C_{11}H_{13}BrO$: C, 54.79; H, 5.43%. Found: C, 54.43; H, 5.39%.

Step (3) Preparation of 1-Bromo-7-methylnaphthalene

According to the procedure of H. Fu, et al., *Tetrahedron Lett.* 3217 (1974), a mixture of triphenylmethanol (138.2 g, 0.531 mol), 8-bromo-2-hydroxy-2-methyl-1,2,3,4-tetrahydronaphthalene (116.4 g, 0.483 mol), and trifluoroacetic acid (338 mL) was stirred at room temperature for 2 days. The mixture was extracted with hexane (500 mL and 250 mL). The combined extracts were washed with $H_2O$ (2×500 mL), saturated aqueous $NaHCO_3$ (500 mL), brine (500 mL), dried ($MgSO_4$), and concentrated to about 200 mL. This solution was left standing until the triphenylmethane crystallized. After filtration, the filtrate was concentrated and purified by flash chromatography ($SiO_2$, eluant: hexane) to give a colorless oil (72.2 g, 70%). An analytical sample was obtained from 200 mg of similarly prepared material by Kugelrohr distillation.

NMR (DMSO-$d_6$, 400 MHz): δ2.53 (s, 3H), 7.36 (m, 1H), 7.46 (dd, $J_1$=8.6 Hz, $J_2$=1.0 Hz, 1H), 7.83 (dd, $J_1$=7.4 Hz, $J_2$=1.0 Hz, 1H), 7.91 (m, 3H).

IR (KBr, $cm^{-1}$): 3050 (CH).

MS: m/e 220 ($M^+$), 141 ($M^+$-Br).

Anal. Calcd for $C_{11}H_9Br$: C, 59.75; H, 4.10%. Found: C, 59.68; H, 4.15%.

Step (4) Preparation of 8-Bromo-2-bromomethylnaphthalene

To boiling $CCl_4$ (250 mL) was added NBS (20.4 g, 0.114 mol) and AIBN (1.4 g, 0.009 mol). After 1 minute, a solution of 1-bromo-7-methylnaphthalene (24.1 g, 0.109 mol) in $CCl_4$ (15 mL) was added all at once. Within 1 minute, the reaction became quite exothermic and the heating mantle was removed for several minutes. Heating was resumed for 30 minutes. The mixture was cooled, filtered, and the filtrate was concentrated to give an off-white solid (32.7 g). The product ws combined with similarly prepared material (32.6 g) and recrystallized from ethyl acetate/hexane to give the product (29.6 g, 45%).

NMR (DMSO-$d_6$, 300 MHz): δ4.99 (s, 2H), 7.48 (m, 1H), 7.68 (dd, J=8.7 Hz, 1.8 Hz, 1H), 7.93 (dd, J=7.5 Hz, 0.9 Hz, 1H), 8.00 (d, J=7.8 Hz, 1H), 8.03 (d, J=8.7 Hz, 1H), 8.23 (s, 1H).

Step (5) Preparation of 8-Bromo-2-naphthalenylacetonitrile

To a stirred partial solution of 8-bromo-2-bromomethylnaphthalene (29.6 g, 0.0987 mol) in acetonitrile (180 mL) was added a solution of NaCN (5.8 g, 0.118 mol) in $H_2O$ (20 mL). The resulting mixture was heated under reflux for 1 hour 20 minutes. The mixture was cooled, concentrated, and partitioned between ether and $H_2O$. The organic phase was washed with $H_2O$, saturated aqueous $NaHCO_3$, brine, dried ($MgSO_4$), and concentrated to give a pale yellow solid (24.1 g, 99%). An analytical sample was obtained by recrystallization of 100 mg of similarly prepared material from toluene/hexane, m.p. 56° C.

NMR (DMSO-$d_6$, 400 MHz): δ4.32 (s, 2H), 7.46 (m, 1H), 7.58 (dd, J=8.4 Hz, 1.7 Hz, 1H), 7.92 (dd, J=7.5 Hz, 1.0 Hz, 1H), 8.00 (d, J=8.4 Hz, 1H), 8.04 (d, J=8.4 Hz, 1H), 8.14 (s, 1H).

IR (KBr, $cm^{-1}$): 2250 (CN).

MS: m/e 245 ($M^+$), 166 ($M^+$-Br).

Anal. Calcd for $C_{12}H_8BrN$: C, 58.56; H, 3.28; N, 5.69%. Found: C, 58.69; H, 3.28; N, 5.51%.

Step (6) Preparation of N'-Hydroxy-2-(8-bromonaphthalenyl)ethanimidamide

To a stirred solution of 8-bromo-2-naphthalenylacetonitrile (24.1 g, 0.0979 mol) and hydroxylamine hydrochloride (13.6 g, 0.196 mol) in DMSO (150 mL) was added NaOMe (25 wt % in MeOH; 4.48 mL, 0.196 mol). The resulting mixture was heated to 80° C. for 1 hour 30 minutes. The MeOH was removed by rotary evaporation and $H_2O$ (400 mL) was added to the remaining mixture. After 30 minutes, the resulting solid was collected by filtration and recrystallized from toluene to give a white solid (20.8 g, 76%). An analytical sample was obtained from previously prepared material by recrystallization from toluene, m.p. 121°-122° C.

NMR (DMSO-$d_6$, 400 MHz): δ3.50 (s, 2H), 5.54 (br s, 2H), 7.38 (m, 1H), 7.54 (dd, J=8.4 Hz, 1.5 Hz, 1H), 7.85 (dd, J=7.4 Hz, 0.8 Hz, 1H), 7.93 (m, 2H), 8.03 (s, 1H), 8.98 (s, 1H).

IR (KBr, $cm^{-1}$): 3440, 3300 (NH and OH), 1650 (C=N).

MS: m/e 278 ($M^+$).

Anal. Calcd for $C_{12}H_{11}BrN_2O$: C, 51.63; H, 3.97; N, 10.03%. Found: C, 51.56; H, 3.90; N, 9.79%.

Step (7) Preparation of 4-[(8-Bromo-2-naphthalenyl)methyl]-3H-1,2,3,5-oxathiadiazole 2-Oxide To a cooled (−20° C.) stirred suspension of N'-hydroxy-2-(8-bromonaphthalenyl)ethanimidamide (20.8 g, 0.0745 mol) in pyridine (12.0 mL, 0.149 mol) and $CH_2Cl_2$ (75 mL) was added a solution of thionyl chloride (5.7 mL, 0.783 mol) in $CH_2Cl_2$ (25 mL) over 10 minutes. The mixture was allowed to warm to −5° C. over 40 minutes (all material went into solution). $H_2O$ (200 mL) was added and the resulting precipitate was collected by filtration. Recrystallization from ethanol (50 mL) gave an off-white solid (12.7 g, 53%). Analytical data for previously prepared material follows, m.p. 159°-160° C.

NMR (DMSO-$d_6$, 400 MHz): δ4.20 (s, 2H), 7.43 (m, 1H), 7.52 (dd, J=8.4 Hz, 1.6 Hz, 1H), 7.89 (dd, J=7.5 Hz, 0.8 Hz, 1H), 7.97 (d, J=8.4 Hz, 1H), 7.99 (d, J=8.5 Hz, 1H), 8.10 (s, 1H), 11.53 (br s, 1H).

IR (KBr, $cm^{-1}$): 1600 (C=N).

MS: m/e 324 ($M^+$).

Anal. Calcd for $C_{12}H_9BrN_2O_2S$: C, 44.32; H, 2.79; N, 8.61%. Found: C, 44.10; H, 2.56; N, 8.34%.

EXAMPLE 2

4-[(5-Chloro-2-naphthalenyl)methyl]-3H-1,2,3,5-oxathiadiazole 2-Oxide

Step (1) Preparation of Ethyl 5-Amino-2-naphthoate

A suspension of ethyl 5-nitro-2-naphthoate prepared according to Price, et al. *J. Am. Chem. Soc.* 74, 3652 (1952) (8.0 g, 0.0326 mol) in EtOH (200 mL) was hydrogenated over 10% Pd/C (600 mg) at 50 psi for 3 hours 30 minutes. The mixture was filtered through Solka floc and concentrated to give a yellow solid (7.0 g, 100%), m.p. 94°-95° C.

NMR ($CDCl_3$, 200 MHz): δ1.44 (t, J=7.4 Hz, 3H), 4.19 (br s, 2H), 4.54 (q, J=7.4 Hz, 2H), 6.87 (dd, J=7.2 Hz, 1.4 Hz, 1H), 7.34 (dd, J=7.2 Hz, 7.2 Hz, 1H), 7.45 (dd, J=7.2 Hz, 1.4 Hz, 1H), 7.85 (d, J=8.9 Hz, 1H), 8.02 (dd, J=8.9 Hz, 2.0 Hz), 8.55 (d, J=2.0 Hz, 1H).

Step (2) Preparation of 5-Amino-2-naphthoic Acid

A mixture of ethyl 5-amino-2-naphthoate (7.0 g, 0.0325 mol), dioxane (40 ml), and 1N NaOH (39 mL) was stirred at room temperature for 16 hours. The dioxane was removed under reduced pressure, $H_2O$ (50 mL) was added, and the mixture was neutralized with acetic acid (2.23 mL). The resulting brown solid precipitate was collected by filtration to give the desired product (5.4 g, 89%), m.p. 231°-234° C.

NMR (DMSO-$d_6$, 300 MHz): δ6.78 (dd, J=6.9 Hz, 1.5 Hz, 1H), 7.26 (m, 2H), 7.80 (dd, J=9.0 Hz, 1.8 Hz, 1H), 8.14 (d, J=9.0 Hz, 1H), 8.39 (d, J=1.5 Hz, 1H).

Step (3) Preparation of 5-Chloro-2-naphthoic Acid

According to the procedure of W. Adcock, et al. *Aust. J. Chem.*, 18, 1351 (1965), to a cooled (10° C.), stirred solution of $NaNO_2$ (1.19 g, 0.0173 mol) in $H_2SO_4$ (15.6 mL) and HOAc (14.4 mL) [prepared by adding $NaNO_2$ to cooled $H_2SO_4$, heating to dissolve, recooling, and adding HOAc] was added a suspension of 5-amino-2-naphthoic acid (2.70 g, 0.0144 mol) in HOAc (48 mL) over 14 minutes. The resulting solution was slowly added (over 15 minutes) to a heated (60° C.) solution of CuCl (6.28 g, 0.0635 mol) in concentrated HCl (88 mL).

Heating was continued for 30 minutes. The mixture was cooled to 5° C., diluted with $H_2O$ (200 mL), and filtered to give a gray solid (2.5 g). The material was dissolved in hot EtOH, treated with activated charcoal, and recrystallized to give a white solid (1.15 g, 38%), m.p. 263°-265° C.

NMR (DMSO-$d_6$, 400 MHz): δ7.59 (dd, J=7.5 Hz, 7.5 Hz, 1H), 7.83 (dd, J=7.5 Hz, 1.0 Hz, 1H), 8.13 (dd, J=8.7 Hz, 1.4 Hz, 1H), 8.15 (d, J=8.7 Hz, 1H), 8.25 (d, J=8.7 Hz, 1H), 8.68 (d, J=1.4 Hz, 1H).

MS: m/e 206 (100%), 189 (42%), 161 (42%).

Step (4) Preparation of 5-Chloro-2-hydroxymethylnaphthalene

To a cooled (0° C.), stirred suspension of 5-chloro-2-naphthoic acid (1.10 g, 5.32 mmol) in THF (10 mL) was added $BH_3$.THF (1M in THF, 7.50 mL, 7.50 mmol) over 10 minutes. The resulting mixture was then heated under reflux for 1 hour 30 minutes, recooled to 0° C., and saturated aqueous $K_2CO_3$ (4 mL) was added. $H_2O$ (20 mL) was added and the mixture was extracted with ether. The combined extracts were washed with brine, dried ($MgSO_4$), and concentrated to give a pale yellow solid (0.94 g, 97%), m.p. 72°-75° C.

NMR ($CDCl_3$, 200 MHz): δ4.87 (s, 2H), 7.38 (dd, J=7.1 Hz, 7.1 Hz, 7.1 Hz, 1H), 7.58 (m, 2H), 7.75 (d, J=7.9 Hz, 1H), 7.82 (s, 1H), 8.26 (d, J=8.9 Hz, 1H).

Step (5) Preparation of 5-Chloro-2-chloromethylnaphthalene

A mixture of 5-chloro-2-hydroxymethylnaphthalene (0.93 g, 5.12 mmol), triphenylphosphine (1.48 g, 5.64 mmol), $CCl_4$ (0.87 g, 5.64 mmol), and $CH_2Cl_2$ (10 mL) was stirred at room temperature for 2 days, concentrated, and triturated with ether. The filtrate was concentrated to give a pale yellow solid (1.37 g). NMR analysis showed the material to contain triphenylphosphine. The product was used without further purification in the next step.

NMR (DMSO-$d_6$, 300 MHz): δ4.96 (s, 2H), 7.72 (m, 2H), 7.93 (m, 3H), 8.08 (d, J=1.2 Hz, 1H), 8.19 (d, J=9.0 Hz, 1H).

Step (6) Preparation of 5-Chloro-2-naphthalenylacetonitrile

A mixture of 5-chloro-2-chloromethylnaphthalene (1.37 g crude product, 5.12 mmol), NaCN (0.275 g, 5.61 mmol), $CH_3CN$ (10 mL), and $H_2O$ (1 mL) was heated under reflux for 5.5 hours, cooled, and stirred at room temperature overnight. The mixture was partitioned between ether and $H_2O$. The aqueous phase was extracted with ether, and the combined ether layers were washed with brine, dried ($MgSO_4$), and concentrated in vacuo. Purification by flash chromatography (eluant EtOAc/hexane (10:90)) gave a pale yellow solid (600 mg, 58%), m.p. 95°-98° C.

NMR ($CDCl_3$, 300 MHz): δ3.91 (s, 2H), 7.41 (m, 2H), 7.73 (d, J=8.1 Hz, 1H), 7.81 (m, 2H), 8.26 (d, J=8.7 Hz, 1H).

IR ($CHCl_3$, $cm^{-1}$): 2260 (CN).

Step (7) Preparation of N'-Hydroxy-2-(5-chloronaphthalenyl)ethanimidamide

A mixture of NaOMe (25 wt % in MeOH, 1.02 mL, 4.46 mmol), MeOH (4 mL), and hydroxylamine hydrochloride (310 mg, 4.46 mmol) was heated at reflux for 20 minutes. 5-Chloro-2-naphthalenylacetonitrile (600 mg, 2.98 mmol) and additional MeOH (4 mL) were added and heating was continued overnight. Additional hydroxylamine hydrochloride (150 mg, 2.16 mmol) and NaOMe (25 wt % in MeOH, 490 μL, 2.14 mmol) were added and heating was resumed for 4 hours. The mixture was cooled, concentrated, and suspended in $H_2O$. The solid was collected by filtration and triturated with ether to give a pale yellow solid (478 mg, 69%), m.p. 121°-125° C.

NMR (DMSO-$d_6$, 300 MHz): δ3.46 (s, 2H), 5.46 (s, 2H), 7.47 (dd, J=7.8 Hz, 7.8 Hz, 1H), 7.60 (m, 2H), 7.86 (m, 2H), 8.08 (d, J=8.7 Hz, 1H), 8.93 (s, 1H).

Step (8) Preparation of 4-[(5-Chloro-2-naphthalenyl)methyl]-3H-1,2,3,5-oxathiadiazole 2-Oxide To a cooled (0° C.), stirred suspension of N'-hydroxy-2-(5-chloronaphthalenyl)ethanimidamide (470 mg, 2.00 mmol) in $CH_2Cl_2$ (3 mL) and pyridine (325 μL, 4.00 mmol) was added thionyl chloride (160 μL, 2.20 mmol) over 2 minutes. The resulting solution was stirred for 25 minutes. $H_2O$ (10 mL) was added and the mixture was extracted with $CH_2Cl_2$ (2×25 mL). The combined extracts were dried ($MgSO_4$) and concentrated. Purification by flash chromatography (eluant EtOAc/hexane (20:80)) and recrystallization from ethanol/ether gave off-white needles (88 mg, 16%), m.p. 164°-165° C.

NMR (DMSO-$d_6$, 400 MHz): δ4.16 (s, 2H), 7.52 (dd, J=7.9 Hz, 7.9 Hz, 1H), 7.61 (dd, J=8.7 Hz, 1.7 Hz, 1H), 7.70 (d, J=7.9 Hz, 1H), 7.90 (d, J=7.9 Hz, 1H), 7.94 (s, 1H), 8.16 (d, J=8.7 Hz, 1H), 11.51 (br s, 1H).

MS: m/e 280 (19%), 175 (100%).

Anal. Calcd for $C_{12}H_9ClN_2O_2S$: C, 51.34; H, 3.23; N, 9.98%. Found: C, 51.26; H, 3.17; N, 9.88%.

EXAMPLE 3

4-[(5-Chloro-2-naphthalenyl)methyl]-3H-1,2,3,5-oxathiadiazole 2-Oxide

Step (1) Preparation of Methyl 5-Bromo-2-naphthoate

To a boiling solution of 2-naphthoic acid (200 g, 1.16 mol) in acetic acid (1000 mL) was added dropwise bromine (60 mL, 2.2 mol) containing 5.0 g of iodine. After the addition was complete, the solution was refluxed for an additional 0.5 hour. After cooling the precipitated product was isolated by filtration, washed with acetic acid and water. The crude acid was treated with hot 1N sodium hydroxide solution (1000 mL). The resulting suspension was filtered to give the sodium salt of the carboxylic acid (107 g). On cooling the filtrate furnished an additional material (43 g, total 150 g). This was suspended in methanol (1 L) and concentrated sulfuric acid (68 mL) was added gradually. This suspension was refluxed for 18 hours. After cooling, the resulting solution was evaporated to dryness in vacuo and the residue partitioned between methylene chloride and water. The aqueous layer was extracted with methylene chloride and the combined organic layers were washed with saturated sodium bicarbonate solution and with water. This was dried ($MgSO_4$) and evaporated in vacuo to give the crude title compound (116.5 g, 38%) as an oil which crystallized slowly on standing to an off-white solid, m.p. 65°-68° C. This compound was pure enough to be used as such in the next step.

Step (2) Preparation of Methyl 5-Chloro-2-naphthoate

According to R. G. R. Bacon, et al., *J. Chem. Soc.* 1097 (1964) and H. Goldstein, et al., *Helv. Chim. Acta.* 21, 62 (1938), a mixture of methyl 5-bromo-2-naphthoate (35.0 g, 0.132 mol), copper (1) chloride (43.1 g, 0.436 mol) and dry DMSO (400 mL) was heated at 105°-110° C. for 6 hours under $N_2$. The mixture was cooled to room temperature, diluted with $H_2O$ (250 mL) and ether (250 mL), and filtered through Celite. The layers were separated, and the organic phase was washed with $H_2O$/brine (1:1), 1NHCl, saturated aqueous $NaHCO_3$, dried ($MgSO_4$), and concentrated to give an off-white solid (28.7 g, 99%). The compound was used without further purification.

NMR (DMSO-$d_6$, 300 MHz): δ3.93 (s, 3H), 7.60 (m, 1H), 7.84 (dd, J=7.5 Hz, 0.9 Hz, 1H), 8.10 (dd, J=8.7 Hz, 1.8 Hz, 1H), 8.15 (d, J=8.4 Hz, 1H), 8.24 (d, J=9.0 Hz, 1H), 8.69 (d, J=1.8 Hz, 1H).

Step (3) Preparation of 5-Chloro-2-hydroxymethylnaphthalene

To a cooled (0° C.) stirred solution of methyl 5-chloro-2-naphthoate (26.7 g, 0.121 mol) in THF (100 mL) was added 1M DIBAL in THF (266 mL, 0.266 mol) over 1 hour 30 minutes. The cooling bath was removed and stirring was continued for 1 hour. The mixture was recooled to 0° C. and 1N NaOH (275 mL) was added (slowly at first). Ether (200 mL) and $H_2O$ (100 mL) were added and the mixture was stirred at room temperature for 1 hour. The layers were separated and the aqueous phase was extracted with ether. The combined extracts were dried ($MgSO_4$) and concentrated to give a white solid (23.2 g, 99%). 200 mg was recrystallized from toluene/hexane for analysis, m.p. 85°-87° C.

NMR (DMSO-$d_6$, 400 MHz): δ4.70 (d, J=5.7 Hz, 2H), 5.42 (t, J=5.7 Hz, 1H), 7.48 (m, 1H), 7.63 (m, 2H), 7.91 (d, J=7.8 Hz, 1H), 7.92 (s, 1H), 8.12 (d, J=8.6 Hz, 1H).

IR (KBr, $cm^{-1}$): 3300 (OH).

MS: m/e 192 (M+), 175 (M+-OH).

Anal. Calcd for $C_{11}H_9ClO$: C, 68.58; H, 4.71%. Found: C, 68.92; H, 4.84%.

Step (4) Preparation of 5-Chloro-2-chloromethylnaphthalene

According to the procedure of T. G. Squires, et al., *J. Org. Chem.* 40, 134 (1975), to a stirred solution of 5-chloro-2-hydroxymethylnaphthalene (17.0 g, 0.0882 mol) in dioxane (100 mL) was added $ZnCL_2$ (360 mg, 2.65 mmol), then thionyl chloride (21.0 g, 0.176 mol) (slightly exothermic). After 40 minutes, the mixture was concentrated, taken up in ether, and washed with saturated aqueous $NaHCO_3$/brine (1:4). The organic phase was dried ($MgSO_4$) and concentrated to give a white solid (18.2 g, 98%). 200 mg was recrystallized from hexane for analysis, m.p. 86°-88° C.

NMR ($CDCl_3$, 400 MHz): δ4.76 (s, 2H), 7.40 (m, 1H), 7.57 (d, J=7.4 Hz, 1H), 7.61 (d, J=8.8 Hz, 1H), 7.75 (d, J=8.2 Hz, 1H), 7.84 (s, 1H), 8.27 (d, J=8.8 Hz, 1H).

IR (KBr, $cm^{-1}$): 2980 (CH).

MS: m/e 210 (M+), 175 (M+-Cl).

Anal. Calcd for $C_{11}H_8Cl_2$: C, 62.59; H, 3.82%. Found: C, 62.47; H, 3.91%.

Step (5) Preparation of 5-Chloro-2-naphthalenylacetonitrile

A mixture of 5-chloro-2-chloromethylnaphthalene (24.5 g, 0.116 mol), sodium cyanide (6.8 g, 0.139 mol), $H_2O$ (25 mL), and acetonitrile (225 mL) was heated under reflux for 6 hours. The mixture was concentrated and suspended in $H_2O$. The solid was collected by filtration, dissolved in acetone, treated with $MgSO_4$, and concentrated to give an off-white solid (22.4 g, 96%). 200 mg was recrystallized from toluene/hexane for analysis, m.p. 110°-111° C. The remaining product was used without further purification.

NMR (DMSO-$d_6$, 400 MHz): δ4.27 (s, 2H), 7.54 (m, 1H), 7.64 (dd, J=8.7 Hz, 1.9 Hz, 1H), 7.71 (dd, J=7.4 Hz, 0.8 Hz, 1H), 7.97 (d, J=8.2 Hz, 1H), 7.99 (s, 1H), 8.20 (d, J=8.7 Hz, 1H).

IR (KBr, $cm^{-1}$): 2240 (CN).

MS: m/e 201 (M+), 166 (M+-Cl).

Anal. Calcd for $C_{12}H_8ClN$: C, 71.47; H, 4.00; N, 6.94%. Found: C, 71.40; H, 3.99; N, 6.78%.

Step (6) Preparation of N'-Hydroxy-2-(5-chloronaphthalenyl)ethanimidamide

To a stirred solution of 5-chloro-2-naphthalenylacetonitrile (5.00 g, 0.0248 mol) and hydroxylamine hydrochloride (3.45 g, 0.0496 mol) in DMSO (50 mL) was added sodium methoxide (25 wt % in MeOH; 11.3 mL, 0.0496 mol). The resulting mixture was heated at 80° C. for 1 hour 30 minutes. The MeOH was removed under reduced pressure and the mixture was diluted with $H_2O$ (150 mL). A white precipitate formed and was collected by filtration (5.04 g, 87%). 200 mg was recrystallized from toluene for analysis, m.p. 133° C.

NMR (DMSO-$d_6$, 400 MHz): δ3.47 (s, 2H), 5.50 (br s, 2H), 7.47 (m, 1H), 7.62 (m, 2H), 7.86 (d, J=7.1 Hz, 1H), 7.87 (s, 1H), 8.09 (d, J=8.7 Hz, 1H), 8.95 (s, 1H).

IR (KBr, $cm^{-1}$): 3490 and 3380 (NH, OH), 1660 (C=N).

MS: m/e 234 (M+), 217 (M+-OH).

Anal. Calcd for $C_{12}H_{11}ClN_2O$: C, 61.48; H, 4.72; N, 11.94%. Found: C, 61.44; H, 5.01; N, 11.71%.

Step (7) Preparation of 4-[(5-Chloro-2-naphthalenyl)methyl]-3H-1,2,3,5-oxathiadiazole 2-Oxide To a cooled (0° C.) stirred suspension of N'-hydroxy-2-(5-chloronaphthalenyl)ethanimidamide (4.8 g, 0.0205 mol) in dichloromethane (30 mL) was added pyridine (3.2 g, 0.0409 mol) all at once and a solution of thionyl chloride (2.7 g, 0.0225 mol) in dichloromethane (10 mL) over 5 minutes. After 25 minutes, $H_2O$ (150 mL) was added and the resulting yellow solid was collected by filtration (4.5 g). The crude product was recrystallized from iPrOH (35 mL) to give an off-white solid (3.5 g, 61%) m.p. 169°-170° C.

NMR (DMSO-$d_6$, 400 MHz): δ4.16 (s, 2H), 7.52 (m, 1H), 7.61 (dd, J=8.7 Hz, 1.7 Hz, 1H), 7.69 (dd, J=7.5 Hz, 1.0 Hz, 1H), 7.90 (d, J=8.3 Hz, 1H), 7.94 (s, 1H), 8.16 (d, J=8.7 Hz, 1H), 11.52 (s, 1H).

IR (KBr, $cm^{-1}$): 3400 (NH).

MS: m/e 280 (M+).

Anal. Calcd for $C_{12}H_9ClN_2O_2S$: C, 51.34; H, 3.23; N, 9.98%. Found: C, 51.24; H, 3.35; N, 9.68%.

We claim:

1. The process for producing compounds of formula (I)

(I)

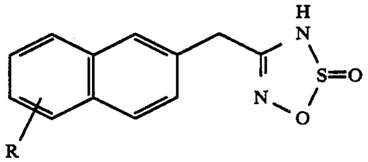

wherein R is hydrogen, lower alkyl containing 1 to 6 carbon atoms, alkoxy containing 1 to 6 carbon atoms, or halogen, and the pharmaceutically acceptable salts thereof which comprises (a) reacting the phenylacetic acid of structure

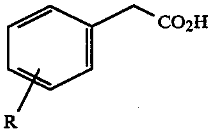

wherein R is as defined above with thionyl chloride to produce the corresponding acid chloride; and reacting said acid chloride with a Lewis acid selected from the group consisting of titanium tetrachloride and aluminum trichloride and ethylene to produce the 2-tetralone of structure

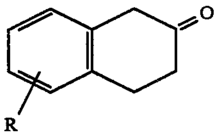

wherein R is as defined above; and (b) reacting said 2-tetralone with an organometallic species selected from the group consisting of methyl magnesium iodide, methyl cerium dichloride and methyl titanium trichloride to produce the tetrahydronaphthol of structure

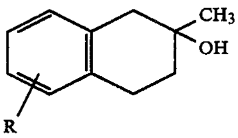

wherein R is as defined above; and (c) reacting said tetrahydronaphthol with trityl alcohol in trifluoroacetic acid or tritylfluoroborate to produce the 2-methylnaphthalene of structure

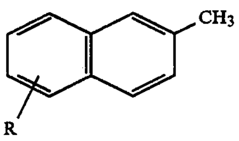

wherein R is as defined above; and (d) reacting said 2-methylnaphthalene with N-bromosuccinimide or N-chlorosuccinimide to produce the 2-halomethylnaphthalene of structure

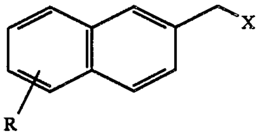

wherein R is as defined above and X is bromine or chlorine; and (e) reacting said 2-halomethylnaphthalene with lithium cyanide, sodium cyanide or potassium cyanide to produce the nitrile of structure

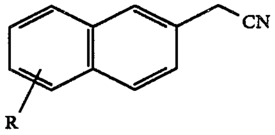

wherein R is as defined above; and (f) reacting said nitrile with hydroxylamine to produce the imidamide of structure

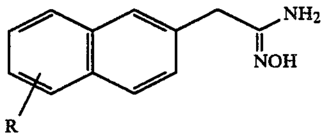

wherein R is as defined above; and (g) reacting said imidamide with thionyl chloride.

2. The process for producing compounds of formula (I)

(I)

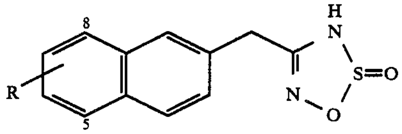

wherein R is bromine or chlorine at position 5 or 8 and pharmaceutically acceptable salts thereof which comprises (a) reacting the naphthoic acid of structure

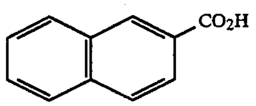

with nitric acid, esterifying the resulting nitronaphthoic acids with ethanol and separating the isomers by recrystallization and chromatography on silica gel to produce the nitronaphthoic acid esters of structure

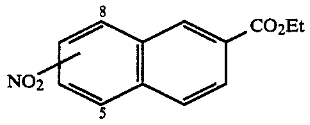

wherein the nitro group is at position 5 or 8; and (b) reacting said nitronaphthoic acid esters with hydrogen and a palladium catalyst to produce the aminonaphthoic acid esters of structure

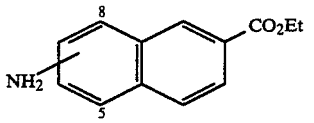

wherein the amino group is at position 5 or 8; and
(c) reacting said aminonaphthoic acid esters with aqueous hydroxide to produce the aminonaphthoic acid esters of structure

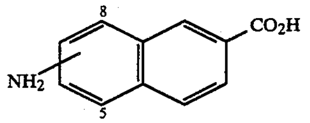

wherein the amino group is at position 5 or 8; and
(d) reacting said aminonaphthoic acids with sodium nitrite and cuprous bromide or cuprous chloride to produce the halonaphthoic acids of structure

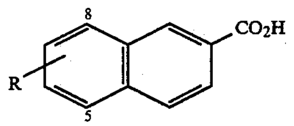

wherein R is bromine or chlorine at position 5 or 8; and
(e) reacting said halonaphthoic acids with a reducing agent selected from the group consisting of borane and lithium aluminum hydride to produce the hydroxymethylnaphthalenes of structure

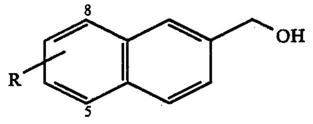

wherein R is bromine or chlorine at position 5 or 8; and
(f) reacting said hydroxymethylnaphthalenes with tri-n-butylphosphine, carbon tetrachloride and potassium cyanide to produce in one step; or with triphenylphosphine and carbon tetrachloride or carbon tetrabromide, or with thionyl chloride and zinc chloride, or with phosphorus tribromide and subsequently with lithium cyanide or sodium cyanide or potassium cyanide to produce in two steps the nitriles of structure

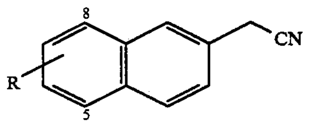

wherein R is bromine or chlorine at position 5 or 8; and
(g) reacting said nitrile with hydroxylamine to produce the imidamide of structure

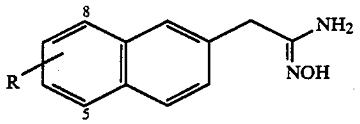

wherein R is bromine or chlorine at position 5 or 8; and
(h) reacting said imidamide with thionyl chloride.

3. The process for producing compounds of formula (I)

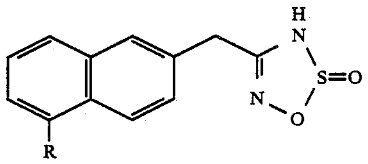

wherein R is bromine or chlorine and the pharmaceutically acceptable salts thereof which comprises
(a) reacting the naphthoic acid of structure

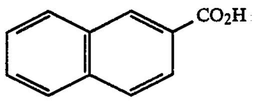

with bromine and esterifying the resulting bromonaphthoic acid to produce the bromonaphthoic acid ester of structure

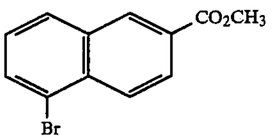

and
(b) reacting said bromonaphthoic acid ester with cuprous chloride to produce the chloronaphthoic acid ester of structure

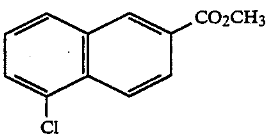

and
(c) reacting said bromo or chloronaphthoic acid ester with a reducing agent selected from the group consisting of lithium aluminum hydride and diisobutyl aluminum hydride to produce the hydroxymethylnaphthalene of structure

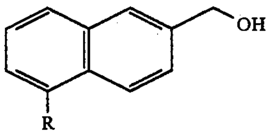

wherein R is as defined above; and (d) reacting said hydroxymethylnaphthalene with phosphorus tribromide or thionyl chloride and zinc chloride, or triphenylphosphine and carbon tetrabromide or carbon tetrachloride to produce the halomethylnaphthalene of structure

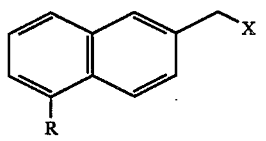

wherein R is as defined above and X is bromine or chlorine; and (e) reacting said halomethylnaphthalene with lithium cyanide, sodium cyanide or potassium cyanide to produce the nitrile of structure

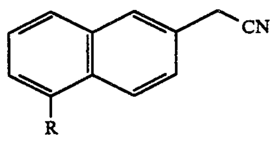

wherein R is as defined above; and (f) reacting said nitrile with hydroxylamine to produce the imidamide of structure

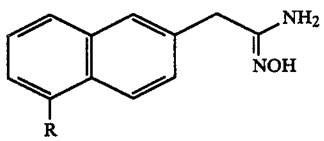

wherein R is as defined above; and (g) reacting said imidamide with thionyl chloride.

* * * * *